United States Patent
Backes

(10) Patent No.: US 7,804,055 B2
(45) Date of Patent: *Sep. 28, 2010

(54) OPTICAL SENSOR DEVICE FOR THE WINDSHIELD OF A MOTOR VEHICLE HAVING FRESNEL LENS STRUCTURES

(75) Inventor: Ulrich Backes, Radolfzell (DE)

(73) Assignee: TRW Automotive Electronics & Components GmbH, Radolfzell (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/220,002

(22) Filed: Jul. 21, 2008

(65) Prior Publication Data

US 2009/0032689 A1    Feb. 5, 2009

(30) Foreign Application Priority Data

Aug. 1, 2007    (DE)    ........................ 10 2007 036 492

(51) Int. Cl.
G02B 6/42    (2006.01)
(52) U.S. Cl. .............................. 250/227.25; 250/227.24
(58) Field of Classification Search ............ 250/227.25, 250/227.14, 227.24, 227.29, 227.3, 222.1, 250/574; 318/484, 444; 340/602
See application file for complete search history.

(56) References Cited

U.S. PATENT DOCUMENTS

| 4,936,657 | A |   | 6/1990 | Tejima et al. |   |
|---|---|---|---|---|---|
| 5,498,866 | A | * | 3/1996 | Bendicks et al. | ....... 250/227.25 |
| 5,898,183 | A | * | 4/1999 | Teder | ........................ 250/574 |
| 6,064,059 | A |   | 5/2000 | Picntka et al. |   |
| 7,236,249 | B1 |   | 6/2007 | Michenfelder et al. |   |
| 2004/0113105 | A1 |   | 6/2004 | Sautter et al. |   |
| 2006/0043322 | A1 |   | 3/2006 | Ishikawa |   |

FOREIGN PATENT DOCUMENTS

| DE | 3624188 | 3/1991 |
|---|---|---|
| DE | 19701258 | 7/1997 |
| DE | 19608648 | 10/1997 |
| DE | 19830120 | 2/1999 |
| EP | 1068112 | 1/2001 |
| JP | S59(1984)144585 | 9/1984 |
| JP | 63038270 | 2/1988 |
| JP | 04147019 | 5/1992 |
| JP | 05150299 | 6/1993 |
| JP | 2000136998 | 5/2000 |
| JP | 200671491 | 3/2006 |
| JP | 2006119032 | 5/2006 |
| WO | 0041009 | 7/2000 |
| WO | 0070404 | 11/2000 |
| WO | 03026937 | 4/2003 |
| WO | 2006005558 | 1/2006 |

* cited by examiner

*Primary Examiner*—Que T Le
(74) *Attorney, Agent, or Firm*—Tarolli, Sundheim, Covell & Tummino LLP

(57) ABSTRACT

An optical sensor device has a sensor unit, which includes a light transmitter, a light receiver and a lens plate, with which a beam of light emitted by the light transmitter is coupled into the window pane, coupled out of the window pane and directed onto the light receiver. On its surface facing the light transmitter and the light receiver, the lens plate includes Fresnel lens structures, and on the opposite surface facing the window pane it includes Fresnel reflector structures. This embodiment is particularly useful as rain sensor. Without light transmitter, the sensor device can be used as a light sensor.

30 Claims, 4 Drawing Sheets a)

b)

c)

OPTICAL SENSOR DEVICE FOR THE WINDSHIELD OF A MOTOR VEHICLE HAVING FRESNEL LENS STRUCTURES

BACKGROUND OF THE INVENTION

This invention relates to an optical sensor device which can be coupled to a window pane, in particular to a windshield of a motor vehicle.

Such sensor devices chiefly are used as rain sensors in motor vehicles for automatically actuating the wipers and as light sensors for controlling the vehicle lighting. The use of classical lenses for influencing the optical path, such as the lenses inclined towards the windshield of the rain sensor disclosed in EP 1 068 112 B1, requires a relatively large packaging space.

As known e.g. from WO 03/026937 A1, smaller constructions are possible by using holographic structures. These sensors are based on the principle of the diffraction of light by means of diffractive elements and therefore have the principal disadvantage of a much smaller yield of useful light and a higher sensitivity to extraneous light.

As regards an optical sensor device, DE 196 08 648 C1 proposes to form the light entrance and emergence surfaces of the light guide unit as Fresnel lenses. But since the surfaces of the light guide, in which the lenses are formed, are arranged perpendicular to the surface of the window pane, the required packaging space of this device is very large.

SUMMARY OF THE INVENTION

The invention provides an optical sensor device minimizing the packaging space under optimum optical conditions.

In a first type of the optical sensor device, there is provided a sensor unit which includes a light transmitter, a light receiver and a lens plate with which a beam of light emitted by the light transmitter is coupled into the window pane, coupled out of the window pane and directed onto the light receiver. On its surface facing the light transmitter and the light receiver, the lens plate includes Fresnel lens structures, and on the opposite surface facing the window pane it includes Fresnel reflector structures. This type is particularly useful as rain sensor. In this case, the sensor unit has two separate Fresnel lens structures with opposed Fresnel reflector structures adjacent to each other in the lens plate. In the focus of the one Fresnel lens structure, the light transmitter is disposed, and in the focus of the other Fresnel lens structure, the light receiver is disposed. The beam of light emerging from the light transmitter is aligned in parallel by the one Fresnel lens structure, perpendicularly traverses the lens plate, is directed obliquely against the window pane by the corresponding Fresnel reflector structure and totally reflected by the window pane and is then coupled into the lens plate by the Fresnel reflector structure belonging to the other Fresnel lens structure and perpendicularly directed through the lens plate onto the other Fresnel lens structure and thereby concentrated on the light receiver. Since all optically active elements are concentrated in the lens plate, a minimum packaging size is obtained. At the same time, a large useful sensor surface is achieved on the window pane.

In a second type of the optical sensor device, a sensor unit is provided, which includes a light receiver and a lens plate by means of which a beam of light impinging on the window pane is coupled out of the window pane and directed onto the light receiver. On its surface facing the light receiver, the lens plate has Fresnel lens structures, and on the opposite surface facing the window pane it has Fresnel reflector structures. This type is particularly useful as light sensor. In this case, a beam of light impinging on the window pane in parallel traverses the same obliquely and is then coupled into the lens plate by the Fresnel reflector structure and perpendicularly directed through the lens plate onto the Fresnel lens structure and thereby concentrated on the light receiver. Here as well, all optically active elements are concentrated in the lens plate, so that a minimum packaging size is obtained. At the same time, an excellent directivity is achieved for the light to be detected.

In an advantageous embodiment of a rain/light sensor, both types of the optical sensor device are combined and share a common lens plate in which all Fresnel lens structures and Fresnel reflector structures are formed.

SHORT DESCRIPTION OF DRAWINGS

Further advantageous and expedient aspects of the optical sensor device in accordance with the invention can be taken from the dependent claims.

The invention will subsequently be explained in detail by means of preferred embodiments with reference to the attached drawings, in which.

DESCRIPTION OF PREFERRED EMBODIMENTS

Figure 1:
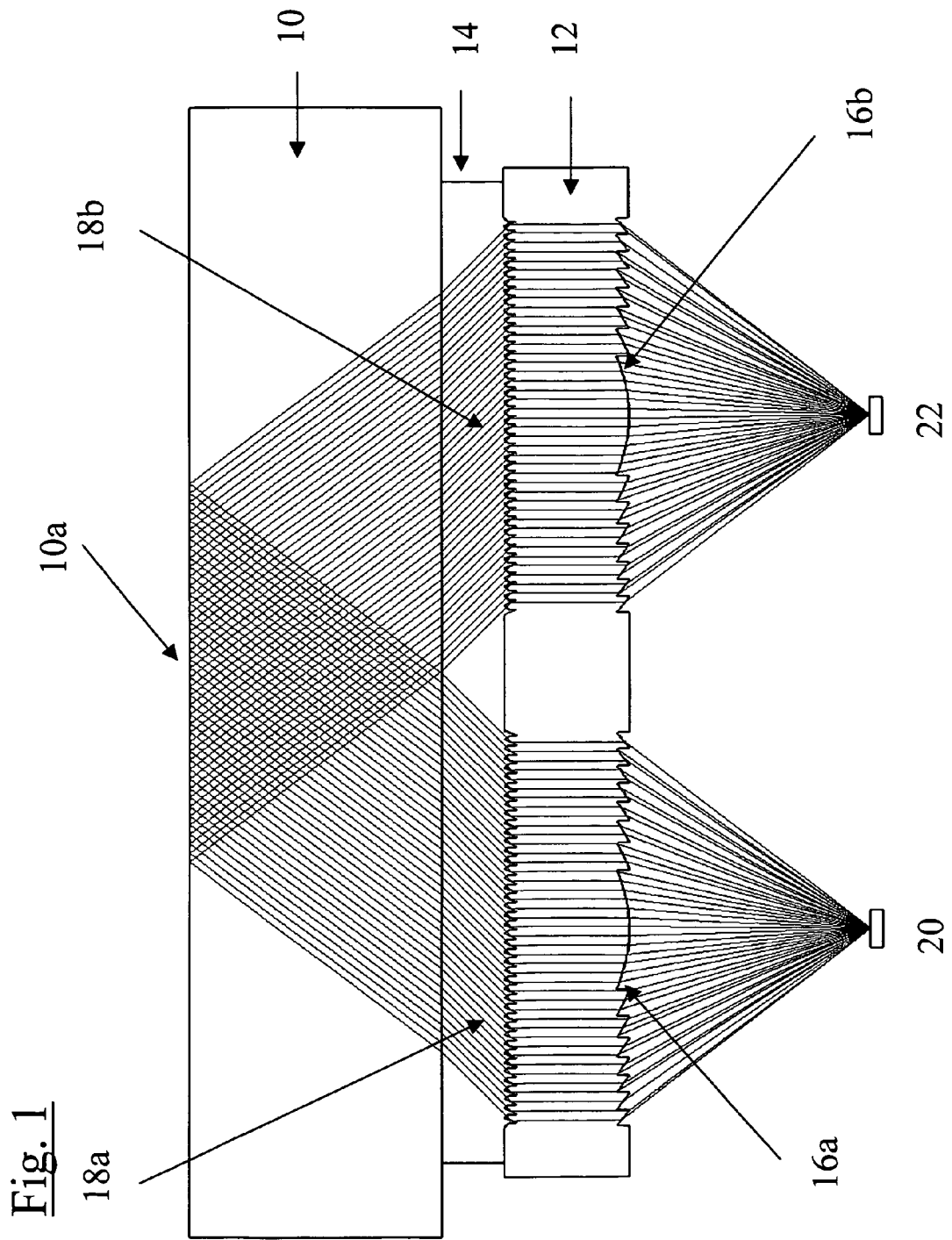
FIG. 1 shows a schematic sectional view of a sensor unit of a rain sensor.

A rain sensor typically consists of two identical optical sensor units. Such sensor unit is schematically shown in FIG. 1. The sensor unit is mounted on the windshield 10 of a motor vehicle. The optically active element of the sensor unit is a lens plate 12. The lens plate 12 is optically coupled to the windshield 10 by means of a coupling layer 14. On its surface facing away from the windshield 10, the lens plate 12 is provided with two identical Fresnel lens structures 16a, 16b, which have a small distance from each other. On its surface facing the windshield 10, the lens plate 12 is provided with two mirror-symmetrical Fresnel reflector structures 18a, 18b in opposition to the Fresnel lens structures 16a, 16b. In the focus of the Fresnel lens structure 16a, a light transmitter 20 is disposed. In the focus of the Fresnel lens structure 16b, a light receiver 22 is disposed.

The beam of light emerging from the light transmitter 20 is transformed by the Fresnel lens structure 16a into parallel light which perpendicularly traverses the lens plate 12. By the Fresnel reflector structure 18a, the parallel beam of light is reflected obliquely to the plane of the lens plate 12 and enters the coupling layer 14. Upon traversing the coupling layer 14, the beam of light enters the windshield 10 and is totally reflected on its opposed inner surface 10a. Then, it again traverses the windshield 10, enters the coupling layer 14 and is deflected by the Fresnel reflector structure 18b, so that it perpendicularly traverses the lens plate 12. Finally, the Fresnel lens structure 16b transforms the parallel beam of light into a converging beam of light, which impinges on the light receiver 22. The Fresnel reflector structures have some particularities which will now be explained with reference to FIG. 2.

Figure 2:
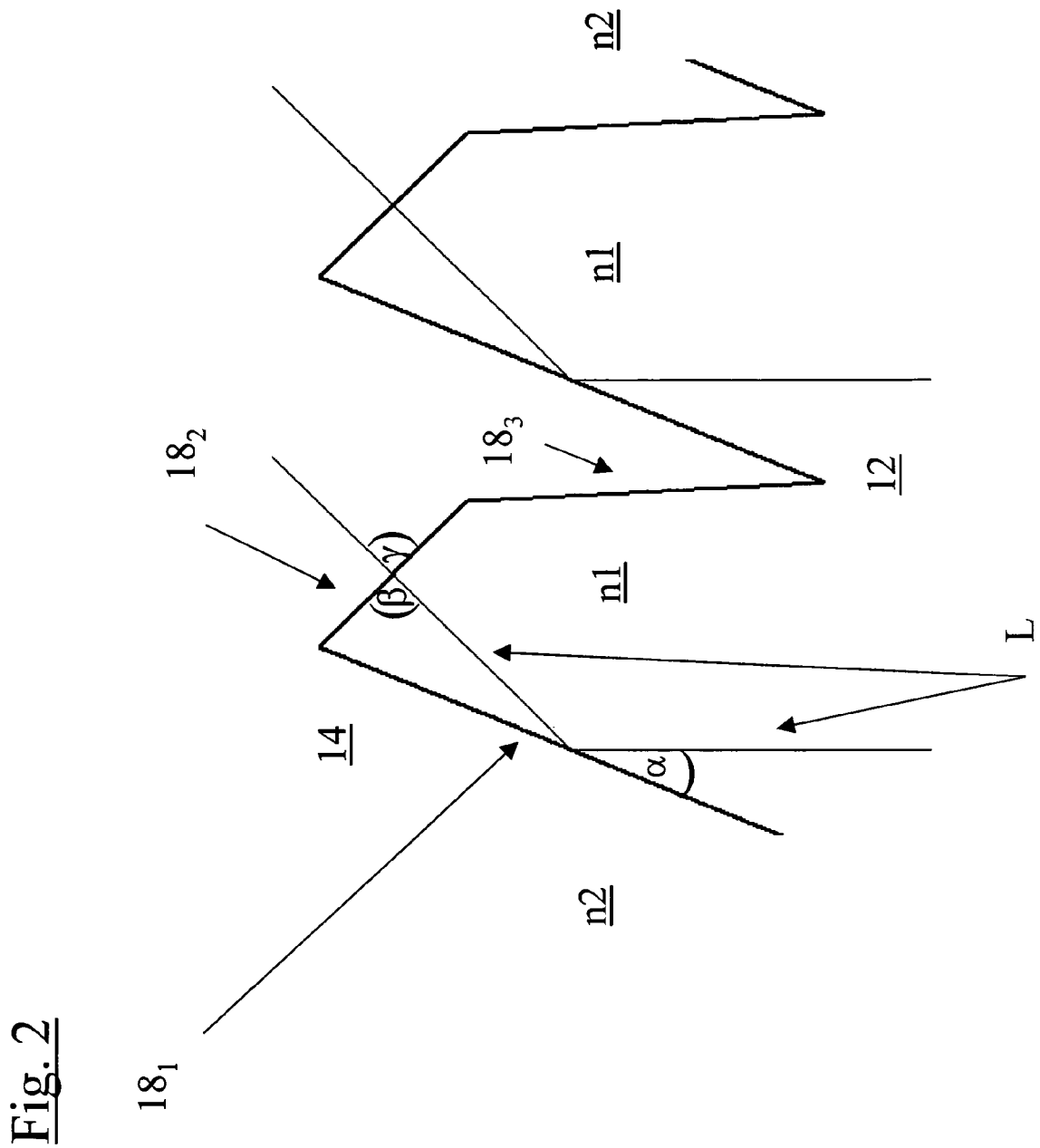
FIG. 2 shows an enlarged cross-sectional view of a Fresnel reflector structure.

Similar to the Fresnel lens structures, the Fresnel reflector structures also consist of fine surface configurations, which alternately are rising and sloping. As shown in FIG. 2, these configurations generally are sawtooth-shaped in cross-section. A first flank $18_1$ continuously extends straight from the base to the peak; a second flank consists of two portions $18_2$ and $18_3$. The portion $18_2$ of the second flank (on the right in FIG. 2) is less steep than the second portion $18_3$, which also is steeper than the flank $18_1$. The refractive indices n1 and n2 of the materials from which the lens plate 12 and the coupling layer 14 are made are carefully adjusted to each other, just as the angles on the flanks of the sawtooth-shaped reflector structures. A beam of light L perpendicularly traversing the lens plate 12 impinges on the flank $18_1$ under an acute angle α, is totally reflected and impinges on the flank $18_2$ under an angle β. In the embodiment shown in FIG. 2, the angle β is 90°, so that the emergence angle γ also is 90°. Thus, there is no refraction of light on the flank $18_2$. The refractive indices n1 and n2 differ only little. A total reflection of the beam of light on the flank $18_1$ occurs on the condition that the angle of incidence is greater than the arc sine of the ratio of the refractive indices. As the ratio of the refractive indices differs only little from 1, the angle of incidence α must be relatively flat. For the pair of materials polycarbonate for the lens plate 12 and silicone rubber for the coupling layer 14, for instance, a maximum angle of incidence α of about 26° is obtained. This angle determines the minimum steepness of the reflector structure. The actual steepness is determined by the fact that the beam of light emerging in the direction of the windshield has the angle necessary for total reflection on the window pane. The angle of incidence desired for total reflection on the window pane typically is about 45°. This angle is compatible with the requirements concerning the geometry of the reflector structures.

FIG. 3a again schematically shows the guidance of light achievable with the geometry of the Fresnel reflector structures as shown in FIG. 2. On the interface between lens plate 12 and coupling layer 14, there is no refraction of light. The consequence is a non-optimum illumination of the sensor surface formed by the totally reflecting surface of the windshield 10.

Figure 3:
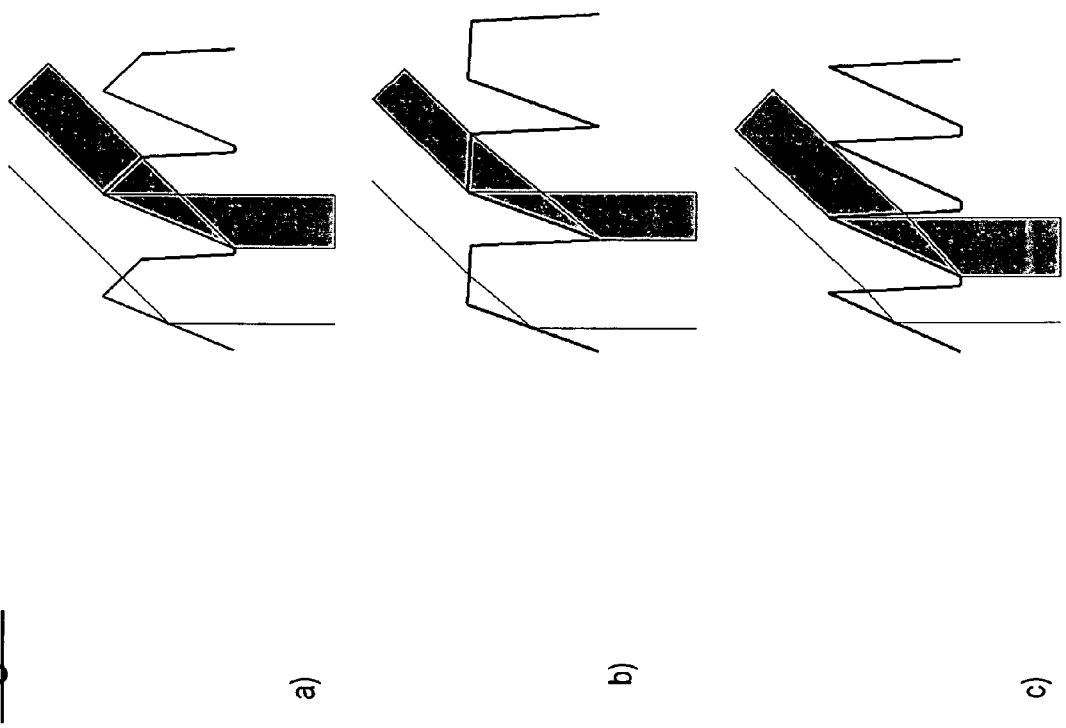
FIGS. 3a to 3c show corresponding cross-sectional views of various embodiments.

The conditions as shown in FIG. 3b are even more unfavorable. In this Figure, the portion $18_2$ on the right-hand flank of the sawtooth structure is even flatter. Since the beams of light impinge on the flank $18_2$ under an angle different from 90°, a refraction of light occurs in a mathematically negative direction (to the right in FIG. 3). The emerging beams of light are even narrower than in FIG. 3a. Optimum conditions are obtained with the geometry as shown in FIG. 3c. Here, the flank of the sawtooth structure shown on the right in this Figure is continuous and set steeper than the left-hand flank. On the right-hand flank, a refraction of light is effected in a mathematically positive sense (to the left in FIG. 3c). The angle of impingement for the light beam on the left-hand flank still is compatible with the condition for total reflection. The beam of light refracted on the right-hand flank just touches the peak of an adjacent sawtooth structure. This results in an uninterrupted illumination of the sensor surface on the windshield.

For the proper function of this embodiment of the Fresnel reflector structures, it is necessary that the material of the coupling layer 14 positively rests against the surface of the reflector structures without any inclusion of air bubbles or the like.

Figure 4:
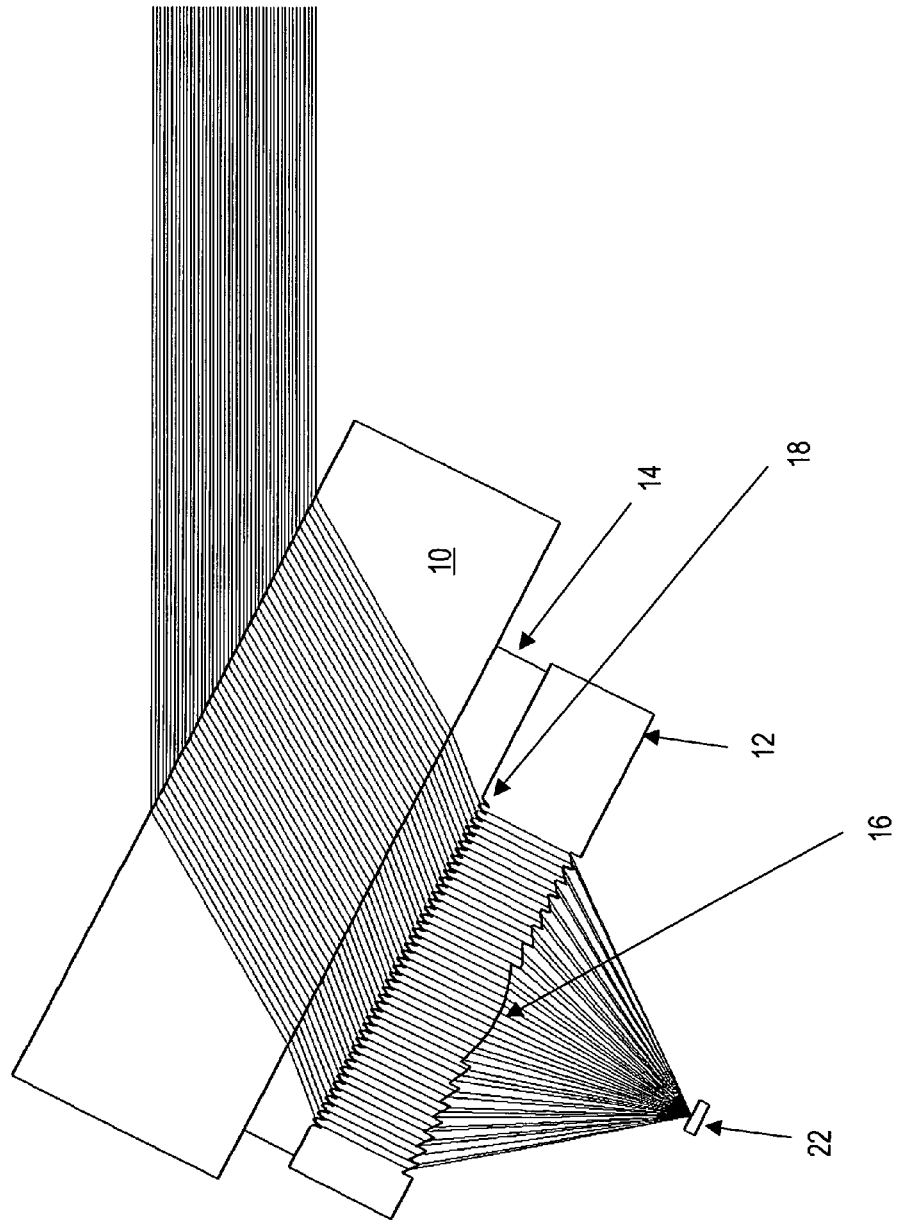
FIG. 4 shows a schematic cross-sectional view of a light sensor.

The embodiment of an optical sensor device as shown in FIG. 4 is a direction-sensitive light sensor. The illustrated sensor unit again has a lens plate 12 as optical element, which in this case only includes a Fresnel lens structure 16 and in opposition thereto a corresponding Fresnel reflector structure 18. The light receiver 22 is placed in the focus of the Fresnel lens structure 16. By means of the coupling layer 14, the lens plate is coupled to the windshield 10, whose angle of inclination is about 27° in the illustrated embodiment. For the geometry of the Fresnel reflector structure 18, the same criteria apply as in the embodiment of a rain sensor as shown in FIG. 1. The light sensor is sensitive to light impinging horizontally on the windshield 10, which is obliquely refracted downwards when impinging on the window pane and through the coupling layer 14 impinges on the Fresnel reflector structure 18, which deflects the beams of light and perpendicularly directs the same through the lens plate 12 onto the Fresnel lens structure 16, which concentrates the light on the light receiver 22.

In practice, combined rain/light sensors are required. The rain sensor includes two identical sensor units of the type shown in FIG. 1. Signal evaluation is effected by forming a difference of the signals supplied by the light receivers. The two sensor units are arranged adjacent to each other and share a common lens plate. The same lens plate also includes the optically active structures of the light sensor shown in FIG. 4. If necessary, further sensors are provided, which can receive light from different directions. Undirected ambient light additionally can be detected through an optically non-active or hardly active region of the lens plate 12.

Manufacturing the lens plate 12 can be effected by a conventional injection molding technique. Alternatively, an embossing technique can be used.

To avoid any malfunction by undesired coupling in and/or out of light, optically non-active surfaces of the lens plate are provided with refractive or reflective structures, e.g. retro-reflector elements (so-called cat's eyes). Light which does not impinge on the optically active surfaces thereby is deflected in "harmless" directions.

The invention claimed is:

1. An optical sensor device adapted to be coupled to a window pane, in particular to a windshield of a motor vehicle, comprising a sensor unit which includes a light transmitter, a light receiver and a lens plate for coupling a beam of light emitted by the light transmitter into the window pane, coupling the beam out of the window pane and directing the beam onto the light receiver, wherein the lens plate has a surface facing the light transmitter and the light receiver and provided with Fresnel lens structures, and an opposite surface facing the window pane and provided with Fresnel reflector structures.

2. The optical sensor device according to claim 1, wherein the surface of the lens plate provided with the reflector structures is coupled to the window pane by a coupling layer positively resting against the reflector.

3. The optical sensor device according to claim 1, wherein the Fresnel reflector structures reflect on an inner surface.

4. The optical sensor device according to claim 1, wherein the lens plate transforms a converging beam of light on the side of the Fresnel lens structures into a parallel beam of light on the side of the Fresnel reflector structures, and vice versa.

5. The optical sensor device according to claim 4, wherein the parallel beam of light traverses the lens plate perpendicularly to said surfaces.

6. The optical sensor device according to claim 5, wherein the parallel beam of light is obliquely inclined with respect to said surfaces of the lens plate.

7. The optical sensor device according to claim 6, wherein outside the lens plate the parallel beam of light is inclined under an angle of about 45° to said surfaces.

8. The optical sensor device according to claim 1, wherein the Fresnel reflector structures generally are sawtooth-shaped in cross-section, with a first flank on which the reflection impinges and a second flank on which a parallel beam of light enters or emerges.

9. The optical sensor device according to claim 8, wherein the second flank of the Fresnel reflector structures is traversed perpendicularly.

10. The optical sensor device according to claim 8, wherein on the second flank of the Fresnel reflector structures a refraction of light is effected.

11. The optical sensor device according to claim 9, wherein the second flank of the Fresnel reflector structures consists of two differently steep portions, the less steep one of which forms an entrance or an emergence surface.

12. The optical sensor device according to claim 10, wherein the second flank of the Fresnel reflector structures consists of two differently steep portions, the less steep one of which forms an entrance or an emergence surface.

13. The optical sensor device according to claim 10, wherein the second flank of the Fresnel reflector structures forms an entrance or an emergence surface which is steeper than the first flank.

14. The optical sensor device according to claim 1, and comprising at least one sensor unit which has two separate Fresnel lens structures with opposed Fresnel reflector structures formed in the lens plate adjacent to each other, the light transmitter being disposed in the focus of a first one of said Fresnel lens structures and the light receiver being disposed in the focus of a second one of said Fresnel lens structures, wherein the beam of light emerging from the light transmitter is aligned in parallel by the first Fresnel lens structure, perpendicularly traverses the lens plate, is obliquely directed against the window pane by the corresponding Fresnel reflector structure and is totally reflected by the window pane and then coupled into the lens plate by the Fresnel reflector structure belonging to the second Fresnel lens structure and perpendicularly directed through the lens plate onto the second Fresnel lens structure and concentrated by the same on the light receiver.

15. The optical sensor device according to claim 14, and including an even number of sensor units, which have a common lens plate.

16. An optical sensor device adapted to be coupled to a window pane, in particular to a windshield of a motor vehicle, comprising a sensor unit which includes a light receiver and a lens plate for coupling a beam of light impinging on the window pane out of the window pane and directing the beam onto the light receiver, wherein the lens plate has a surface facing the light receiver and provided with Fresnel lens structures, and an opposite surface facing the window pane and provided with Fresnel reflector structures.

17. The optical sensor device according to claim 16, wherein the surface of the lens plate provided with the reflector structures is coupled to the window pane by a coupling layer positively resting against the reflector structures.

18. The optical sensor device according to claim 16, wherein the Fresnel reflector structures reflect on an inner surface.

19. The optical sensor device according to claim 16, wherein the lens plate transforms a converging beam of light on the side of the Fresnel lens structures into a parallel beam of light on the side of the Fresnel reflector structures, and vice versa.

20. The optical sensor device according to claim 19, wherein the parallel beam of light traverses the lens plate perpendicularly to said surfaces.

21. The optical sensor device according to claim 19, wherein the parallel beam of light is obliquely inclined with respect to said surfaces of the lens plate.

22. The optical sensor device according to claim 21, wherein outside the lens plate the parallel beam of light is inclined under an angle of about 45° to said surfaces.

23. The optical sensor device according to claim 16, wherein the Fresnel reflector structures generally are sawtooth-shaped in cross-section, with a first flank on which the reflection impinges and a second flank on which a parallel beam of light enters or emerges.

24. The optical sensor device according to claim 23, wherein the second flank of the Fresnel reflector structures is traversed perpendicularly.

25. The optical sensor device according to claim 23, wherein on the second flank of the Fresnel reflector structures a refraction of light is effected.

26. The optical sensor device according to claim 23, wherein the second flank of the Fresnel reflector structures consists of two differently steep portions, the less steep one of which forms an entrance or an emergence surface.

27. The optical sensor device according to claim 23, wherein the second flank of the Fresnel reflector structures consists of two differently steep portions, the less steep one of which forms an entrance or an emergence surface.

28. The optical sensor device according to claim 25, wherein the second flank of the Fresnel reflector structures forms an entrance or an emergence surface which is steeper than the first flank.

29. The optical sensor device according to claim 16, wherein a beam of light impinging on the window pane under a narrow detection angle obliquely traverses the same and then is coupled into the lens plate by the Fresnel reflector structure and perpendicularly directed through the lens plate onto the Fresnel lens structure and thereby concentrated on the light receiver.

30. A combined rain/light sensor, comprising
(i) a first optical sensor device adapted to be coupled to a window pane, in particular to a windshield of a motor vehicle, comprising a sensor unit which includes a light transmitter, a light receiver and a lens plate for coupling a beam of light emitted by the light transmitter into the window pane, coupling the beam out of the window pane and directing the beam onto the light receiver, wherein the lens plate has a surface facing the light transmitter and the light receiver and provided with Fresnel lens structures, and an opposite surface facing the window pane and provided with Fresnel reflector structures; and
(ii) a second optical sensor device adapted to be coupled to a window pane, in particular to a windshield of a motor vehicle, comprising a sensor unit which includes a light receiver and a lens plate for coupling a beam of light impinging on the window pane out of the window pane and directing the beam onto the light receiver, wherein the lens plate has a surface facing the light receiver and provided with Fresnel lens structures, and an opposite surface facing the window pane and provided with Fresnel reflector structures.

* * * * *